US012594039B2

(12) United States Patent
Chung

(10) Patent No.: US 12,594,039 B2
(45) Date of Patent: Apr. 7, 2026

(54) ELECTRONIC DEVICE AND METHOD FOR CORRECTING BIOMETRIC DATA ON BASIS OF DISTANCE BETWEEN ELECTRONIC DEVICE AND USER, MEASURED USING AT LEAST ONE SENSOR

(71) Applicant: Samsung Electronics Co., Ltd., Gyeonggi-do (KR)

(72) Inventor: Sohyun Chung, Gyeonggi-do (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1165 days.

(21) Appl. No.: 17/614,665

(22) PCT Filed: May 8, 2020

(86) PCT No.: PCT/KR2020/006129
§ 371 (c)(1),
(2) Date: Nov. 29, 2021

(87) PCT Pub. No.: WO2020/242087
PCT Pub. Date: Dec. 3, 2020

(65) Prior Publication Data
US 2022/0249027 A1     Aug. 11, 2022

(30) Foreign Application Priority Data

May 31, 2019     (KR) ........................ 10-2019-0064804

(51) Int. Cl.
*A61B 5/00*          (2006.01)
*A61B 5/021*         (2006.01)
(Continued)

(52) U.S. Cl.
CPC ............ *A61B 5/7203* (2013.01); *A61B 5/021* (2013.01); *A61B 5/02416* (2013.01);
(Continued)

(58) Field of Classification Search
CPC ... A61B 5/7203; A61B 5/021; A61B 5/02416; A61B 5/681; A61B 5/6898;
(Continued)

(56) References Cited

U.S. PATENT DOCUMENTS 9,723,997 B1      8/2017  Lamego
2017/0273576 A1   9/2017  Ozawa et al.
(Continued)

FOREIGN PATENT DOCUMENTS

JP      2017-176266 A      10/2017
KR      10-1838813 B1       3/2018
(Continued)

OTHER PUBLICATIONS

Korean Office Action dated May 22, 2024.

*Primary Examiner* — Abid A Mustansir
(74) *Attorney, Agent, or Firm* — Sughrue Mion, PLLC

(57)          ABSTRACT
According to various embodiments of the present invention, an electronic device may comprise a first sensor, a processor operably connected to the first sensor, and a memory operably connected to the processor, wherein the memory stores instructions that, when executed by the processor, cause the electronic device to: when a signal for measuring biometric information is detected, acquire depth information about a user of the electronic device from the first sensor; determine a position of a biometric reference point of the user, on the basis of the acquired depth information about the user; acquire a biometric signal relating to a measurement point of the user from the first sensor; calculate a distance between the measurement point and the biometric reference point; and correct biometric data about the user on the basis of the calculated distance and the acquired biometric signal. In addition to the various embodiments disclosed in the present invention, various other embodiments are also possible.

12 Claims, 11 Drawing Sheets

(51) Int. Cl.

| | |
|---|---|
| *A61B 5/024* | (2006.01) |
| *A61B 5/11* | (2006.01) |
| *G06T 7/50* | (2017.01) |
| *G06V 40/16* | (2022.01) |

(52) U.S. Cl.
CPC ............ *A61B 5/681* (2013.01); *A61B 5/6898* (2013.01); *G06T 7/50* (2017.01); *G06V 40/172* (2022.01); *A61B 5/1102* (2013.01); *G06T 2207/10028* (2013.01)

(58) Field of Classification Search
CPC ... A61B 5/1102; A61B 5/0077; A61B 5/0285; A61B 5/14532; A61B 5/318; A61B 5/7221; A61B 5/0024; G06T 7/50; G06T 2207/10028; G06V 40/172; G06V 10/98
See application file for complete search history.

(56) References Cited

U.S. PATENT DOCUMENTS

| | | | |
|---|---|---|---|
| 2019/0021611 A1 | 1/2019 | Kwon et al. | |
| 2019/0029596 A1 | 1/2019 | Kang et al. | |
| 2019/0038218 A1 | 2/2019 | Chang et al. | |
| 2019/0307339 A1* | 10/2019 | Aelen .................. | A61B 5/7475 |

FOREIGN PATENT DOCUMENTS

| | | |
|---|---|---|
| KR | 10-2019-0011163 A | 2/2019 |
| KR | 10-2019-0011591 A | 2/2019 |
| KR | 10-2019-0013312 A | 2/2019 |

* cited by examiner

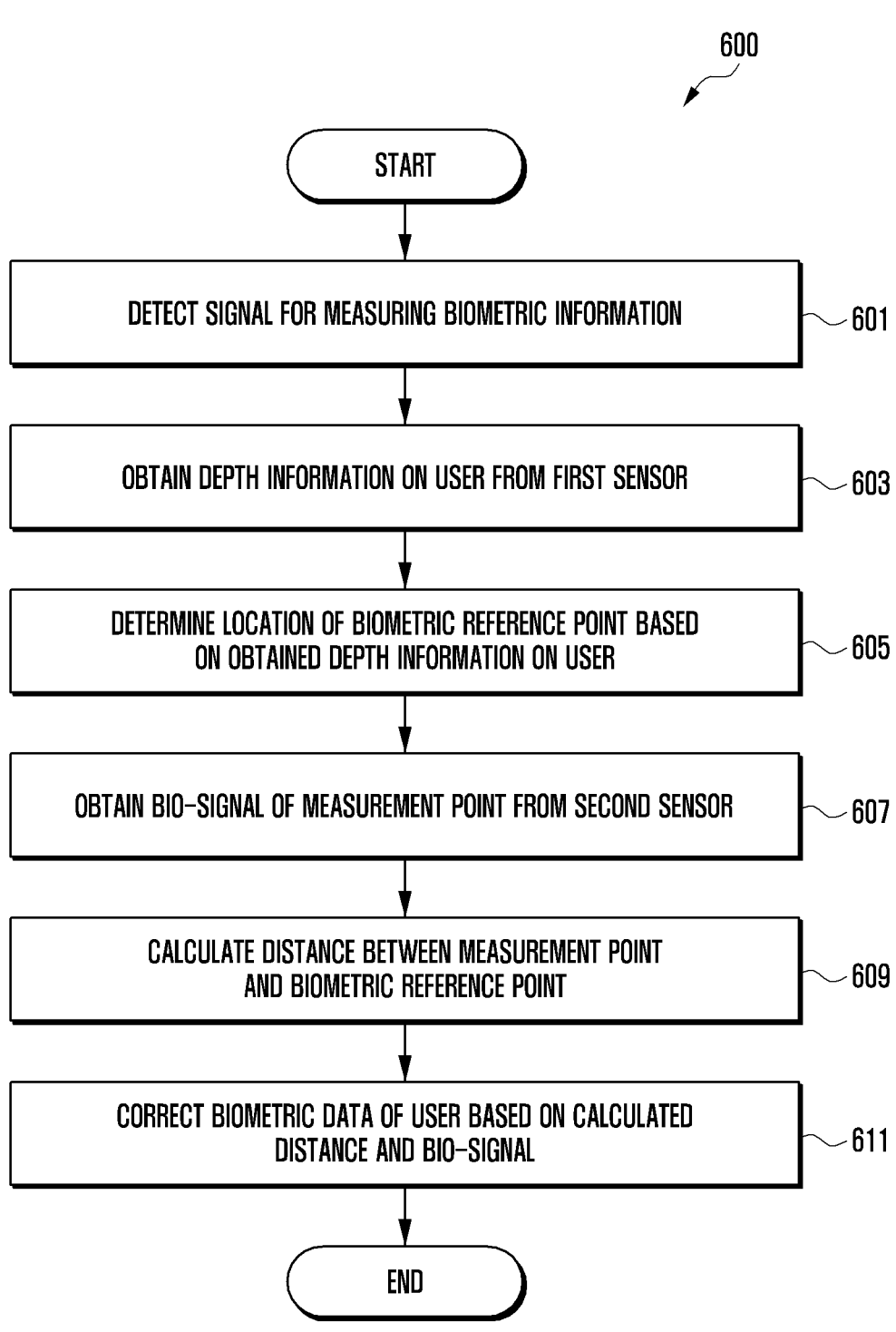

600

START

DETECT SIGNAL FOR MEASURING BIOMETRIC INFORMATION ~601

OBTAIN DEPTH INFORMATION ON USER FROM FIRST SENSOR ~603

DETERMINE LOCATION OF BIOMETRIC REFERENCE POINT BASED
ON OBTAINED DEPTH INFORMATION ON USER ~605

OBTAIN BIO-SIGNAL OF MEASUREMENT POINT FROM SECOND SENSOR ~607

CALCULATE DISTANCE BETWEEN MEASUREMENT POINT
AND BIOMETRIC REFERENCE POINT ~609

CORRECT BIOMETRIC DATA OF USER BASED ON CALCULATED
DISTANCE AND BIO-SIGNAL ~611

END

FIG. 7

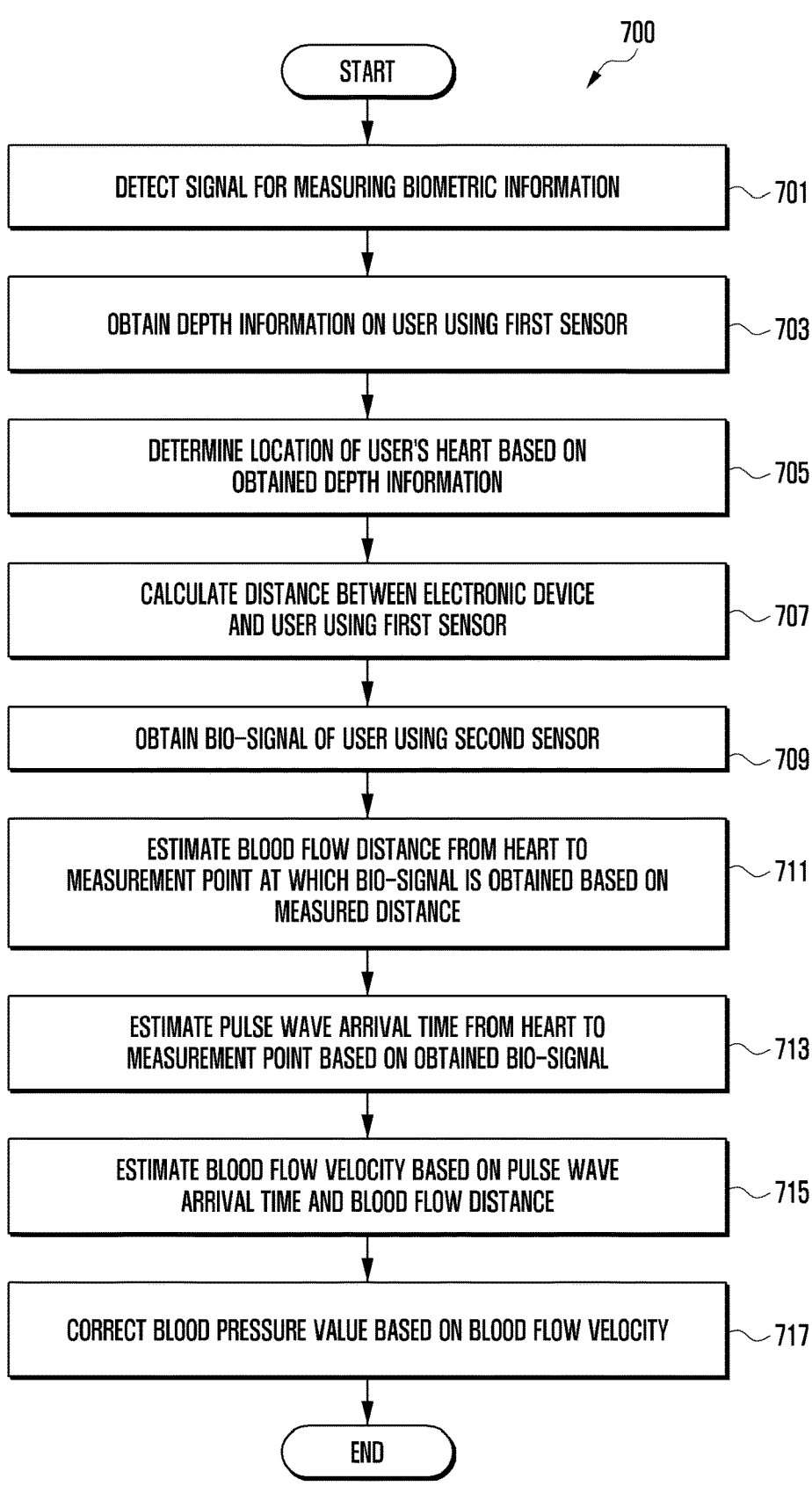

700

START

DETECT SIGNAL FOR MEASURING BIOMETRIC INFORMATION ~701

OBTAIN DEPTH INFORMATION ON USER USING FIRST SENSOR ~703

DETERMINE LOCATION OF USER'S HEART BASED ON
OBTAINED DEPTH INFORMATION ~705

CALCULATE DISTANCE BETWEEN ELECTRONIC DEVICE
AND USER USING FIRST SENSOR ~707

OBTAIN BIO-SIGNAL OF USER USING SECOND SENSOR ~709

ESTIMATE BLOOD FLOW DISTANCE FROM HEART TO
MEASUREMENT POINT AT WHICH BIO-SIGNAL IS OBTAINED BASED ON
MEASURED DISTANCE ~711

ESTIMATE PULSE WAVE ARRIVAL TIME FROM HEART TO
MEASUREMENT POINT BASED ON OBTAINED BIO-SIGNAL ~713

ESTIMATE BLOOD FLOW VELOCITY BASED ON PULSE WAVE
ARRIVAL TIME AND BLOOD FLOW DISTANCE ~715

CORRECT BLOOD PRESSURE VALUE BASED ON BLOOD FLOW VELOCITY ~717

END

ELECTRONIC DEVICE AND METHOD FOR CORRECTING BIOMETRIC DATA ON BASIS OF DISTANCE BETWEEN ELECTRONIC DEVICE AND USER, MEASURED USING AT LEAST ONE SENSOR

CROSS REFERENCE TO RELATED APPLICATIONS

This application is a National Phase Entry of PCT International Application No. PCT/KR2020/006129, which was filed on May 8, 2020, and claims a priority to Korean Patent Application No. 10-2019-0064804, which was filed on May 31, 2019, the contents of which are incorporated herein by reference.

TECHNICAL FIELD

Various embodiments of the disclosure relate to a method of correcting biometric data based on a distance between an electronic device and a user measured using at least one sensor.

BACKGROUND ART

An electronic device may include a biosensor to measure biometric information on a user thereof. For example, the biosensor may include a photoplethysmograph (PPG) sensor, an electrocardiograph (ECG) sensor, and/or a ballistocardiogram (BCG) sensor. The electronic device may obtain biometric information, for example, heartbeat information on a user thereof using the biosensor. By periodically measuring biometric information using the biosensor, the user can manage his or her own health status.

DISCLOSURE OF INVENTION

Technical Problem

Because the electronic device obtains various biometric information (e.g., blood pressure, electrocardiogram, blood sugar, and/or oxygen saturation) as well as heart rate information only with a biosensor provided therein, an error may occur in the biometric information according to a user's condition thereof.

An electronic device according to various embodiments of the disclosure may obtain depth information on an external object using a sensor provided for personal authentication, and calculate distance information to the external object based on the depth information. The electronic device may obtain more accurate biometric information in consideration of not only biometric information obtained through the biosensor in order to obtain biometric information on a user thereof but also a distance calculated using a sensor provided for personal authentication.

Solution to Problem

According to various embodiments of the disclosure, an electronic device includes a first sensor; a processor operatively connected to the first sensor; and a memory operatively connected to the processor, wherein the memory stores instructions that, when executed by the processor, cause the electronic device to obtain depth information on a user of the electronic device from the first sensor when a signal for measuring biometric information is detected, to determine a location of the user's biometric reference point based on the obtained depth information on the user, to obtain a bio-signal of the user's measurement point from the first sensor, to calculate a distance between the measurement point and the biometric reference point, and to correct biometric data of the user based on the calculated distance and the obtained bio-signal.

According to various embodiments of the disclosure, a method of correcting biometric data based on a distance between an electronic device and a user measured using at least one sensor of the electronic device includes obtaining depth information on a user of the electronic device from a first sensor when a signal for measuring biometric information is detected; determining a location of the user's biometric reference point based on the obtained depth information on the user; obtaining a bio-signal of a measurement point of the user from the first sensor; calculating a distance between the measurement point and the biometric reference point; and correcting biometric data of the user based on the calculated distance and the obtained bio-signal.

Advantageous Effects of Invention

An electronic device according to various embodiments of the disclosure can use a sensor used for personal authentication in addition to a biosensor for increasing the accuracy of biometric information. A distance between the electronic device and an external object can be measured through the sensor used for personal authentication, and more diverse and accurate biometric information on a user can be obtained based on the measured distance and biometric information obtained through the biosensor.

BRIEF DESCRIPTION OF DRAWINGS

FIG. 6 is a flowchart illustrating a method in which an electronic device obtains a distance between the electronic device and a user and biometric data using a plurality of sensors according to various embodiments.

FIG. 7 is a flowchart illustrating a method in which an electronic device obtains biometric data using a plurality of sensors according to various embodiments.

MODE FOR THE INVENTION

Figure 1:
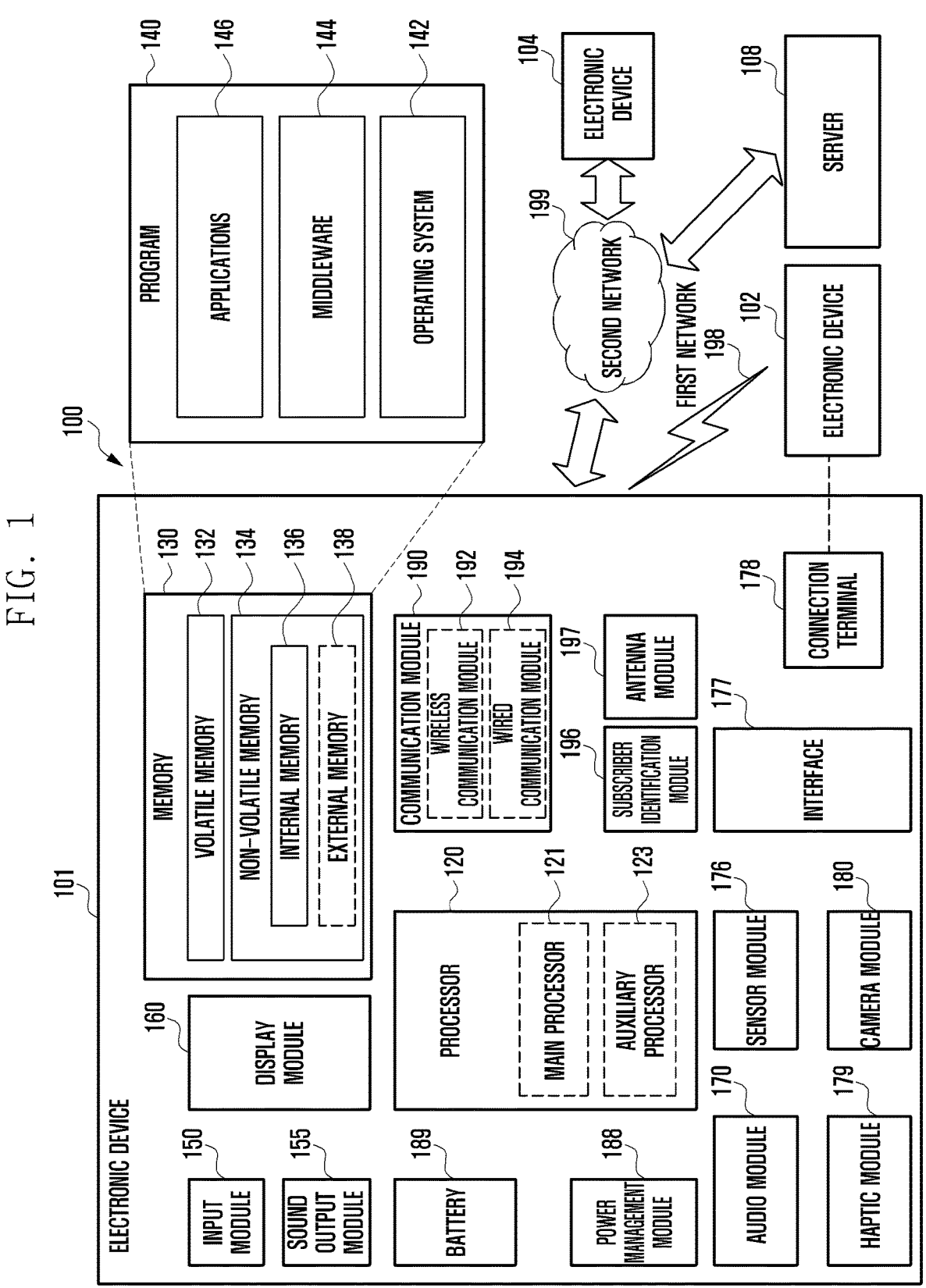
FIG. 1 is a block diagram illustrating an electronic device in a network environment according to various embodiments.

FIG. 1 is a block diagram illustrating an electronic device 101 in a network environment 100 according to various embodiments.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display module 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display module 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display module 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) (e.g., speaker or headphone) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) (e.g., a wireless transceiver) or a wired communication module 194 (e.g., a local area network (LAN) communication module or a power line communication (PLC) module) (e.g., a wired transceiver). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., local area network (LAN) or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
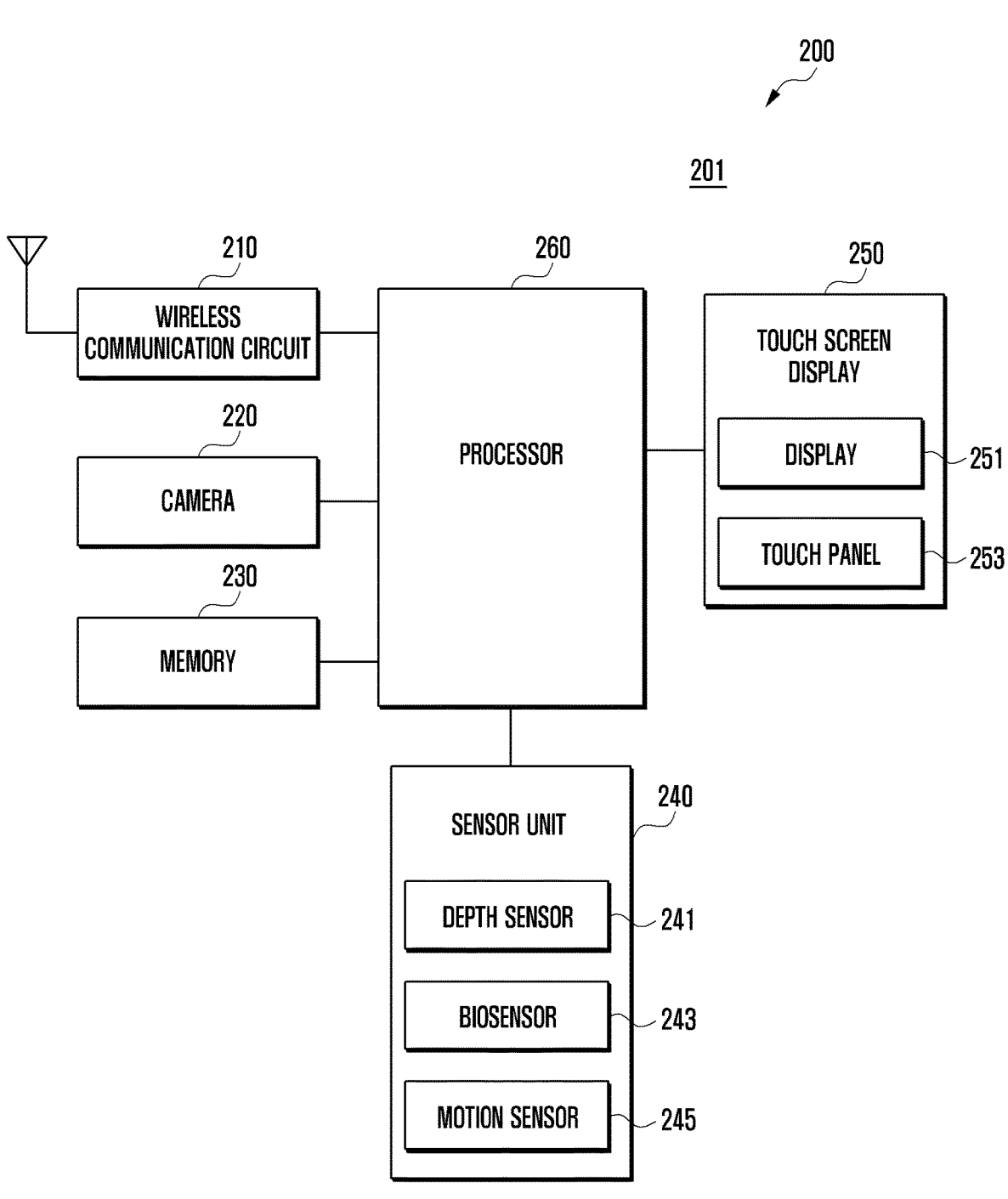
FIG. 2 is a block diagram illustrating an electronic device according to various embodiments.

FIG. 2 is a block diagram 200 illustrating an electronic device 201 according to various embodiments.

Referring to FIG. 2, the electronic device 201 (e.g., the electronic device 101 of FIG. 1) may include a wireless communication circuit 210 (e.g., the communication module 190 of FIG. 1), a camera 220 (e.g., the camera module 180 of FIG. 1), a memory 230 (e.g., the memory 130 of FIG. 1), a sensor unit 240 (e.g., the sensor module 176 of FIG. 1), a touch screen display 250 (e.g., the display module 160 of FIG. 1), and a processor 260 (e.g., the processor 120 of FIG. 1).

According to an embodiment, the wireless communication circuit 210 (e.g., the communication module 190 of FIG. 1) may connect communication between the electronic device 201 (e.g., the electronic device 101 of FIG. 1) and an external electronic device (e.g., the electronic device 102 and the electronic device 104 of FIG. 1) or a server (e.g., the server 108 of FIG. 1).

In an embodiment, the wireless communication circuit 210 may transmit biometric information obtained by the sensor unit 240 to the external electronic device.

According to an embodiment, the camera 220 (e.g., the camera module 180 of FIG. 1) may transfer a collected image to a display 251 as a preview image to enable the user to check an image projected through the camera 220. The camera 220 may include an image sensor that configures an image based on received optical information. The camera 220 may photograph a collected image at a time point in which an input requesting photographing occurs to generate image data in response to the input requesting photographing. In an embodiment, one or more cameras 220 may be provided.

According to an embodiment, the memory 230 (e.g., the memory 130 of FIG. 1) may store a program for obtaining biometric information, a program according to embodiments of the disclosure, and obtained biometric information.

In an embodiment, in order to calculate a distance between the electronic device 201 and an external object, for example, a user (or a distance between a measurement point and a biometric reference point), the memory 230 may store guide information (e.g., guide information for inducing a user to stretch out an arm and take a picture) for inducing a user to take a reference posture.

In an embodiment, the memory 230 may store arm lengths according to gender and age for each range.

According to an embodiment, the sensor unit 240 (e.g., the sensor module 176 of FIG. 1) may detect an external environmental state or a bio-signal of the electronic device 201 and generate an electrical signal or a data value corresponding to the detected state or the detected bio-signal. For example, the sensor unit 240 may include a depth sensor 241, a biosensor 243, and a motion sensor 245.

In an embodiment, the depth sensor 241 may obtain depth information on an external object, for example, a user. The depth sensor 241 may measure distance information between the electronic device 201 and the user. The depth sensor 241 may measure a distance between the electronic device 201 and a specific area of the user as well as a distance between the electronic device 201 and a specific point of the user.

For example, a method of obtaining depth information using the depth sensor 241 may include a time of flight (ToF) method and a structured light (SL) method.

In an embodiment, the ToF sensor may calculate a time difference when light emitted from an emitter is reflected by an external object and a receiver receives the corresponding light, and multiply the calculated time difference by a speed of light to calculate a distance between the electronic device 201 and the external object.

In an embodiment, the structured light sensor may emit a plurality of structured lights having different designated patterns (e.g., patterns of structured light) to an external object (e.g., a user of the electronic device 201), and obtain each of the plurality of emitted structured lights pattern. The structured light sensor may recognize an external object based on distortion of a predetermined pattern formed while a plurality of emitted structured lights are reflected from the external object. For example, the structured light sensor may obtain information on a recognized external object, for example, a location of a user's face, eyes, nose, mouth, and/or upper body depth information based on distortion of a predetermined pattern.

In an embodiment, the depth sensor 241 may estimate a length of the user's arm based on the measured distance, and estimate a length of a blood vessel between a measurement point and a main body point based on the estimated arm length.

In an embodiment, the depth sensor 241 may include an emitter and a receiver. The emitter may emit visible light and/or IR. The receiver may detect incident light applied by being reflected back after light emitted from the emitter reaches an external object. For example, reflected and applied light may be received in the form of a dot or a plane. The depth sensor 241 may measure a distance between the electronic device 201 and a specific point (e.g., eyes, nose, and/or mouth) of the external object based on the received dot form. In another embodiment, the depth sensor 241 may estimate a distance between the electronic device 201 and the external object and a form of the external object based on the received plane form.

In an embodiment, the depth sensor 241 may obtain information related to a user's heartbeat. For example, the depth sensor 241 may measure information related to the user's heartbeat using the camera 220 and an IR light source included in the depth sensor 241. The emitter of the depth sensor 241 may emit IR to the external object, for example, a part of the user's body. The camera 220 may sequentially capture a value in which emitted light is reflected back and applied upon reaching the external object. The depth sensor 241 may obtain information related to a heartbeat according to a change amount of a signal absorbed by hemoglobin of blood included in a blood vessel of a part of an external object, for example, the user's body based on at least one image captured by the camera 220.

In an embodiment, the depth sensor 241 may be included in the camera 220.

In another embodiment, the depth sensor 241 may measure bio-information (e.g., a bio-signal of a measurement point). The depth sensor 241 may obtain other physiological information such as an amount of moisture and fat according to a wavelength band of a used light source.

In another embodiment, the depth sensor 241 may include an iris sensor. The iris sensor may include an emitter and a receiver. In the iris sensor, IR of a specific band emitted by the emitter of the iris sensor may be reflected by the user's iris, and the receiver of the iris sensor may receive the IR, and generate iris information through normalization.

In another embodiment, the depth sensor 241 may emit light from the emitter having a plurality of point light sources to the external object, and the receiver may receive light of the lighted point light source reflected from the external object to generate a three-dimensional (3D) image of the external object. The processor 260 may combine the 3D image and external information (e.g., background information) captured by the camera 220 to generate a 3D animation.

In an embodiment, the depth sensor 241 may include a time of flight (ToF) sensor and/or a structured light sensor. The ToF sensor may calculate a time difference when light emitted from the emitter is reflected by the external object and the receiver receives the corresponding light, and multiply the calculated time difference by a speed of light to calculate a distance between the electronic device 201 and the external object. For example, the ToF sensor may include an indirect ToF (iToF) sensor and a direct ToF (dToF) sensor.

In an embodiment, when the iToF sensor is used, the processor 260 may measure an amplitude and phase of modulated light to calculate quantitative absorption and scattering. The quantitative absorption and scattering values may be used for measuring biometric information, for example, hemoglobin concentration, local fat, body water, and/or blood glucose concentration according to a wavelength of the used light source. When the iToF sensor is used, light emitted to a tissue may be reflected and received, and the processor 260 may measure a change amount in an amplitude and phase of the received modulated light, compared to a reference amplitude and phase. The processor 260 may calculate quantitative absorption and scattering based on the measured amount of change. The processor 260 may obtain information related to the user's biological body based on the quantitative absorption and scattering values calculated using the iToF sensor.

In an embodiment, when the dToF sensor is used, the processor 260 may analyze the spread of light emitted by a pulse to calculate quantitative absorption and scattering values. The processor 260 may obtain information related to the user's biological body based on the quantitative absorption and scattering values calculated using the dToF sensor.

In an embodiment, the biometric information may be measured in a non-contact manner in a state where the sensor and the measurement point are spaced apart, and in this case, a speed of light in the atmosphere may be different from that of light in a living body. The ToF sensor may measure biometric information in a non-contact manner in a state in which the sensor and the measurement point are spaced apart. The measured biometric information may be used for correcting the difference in the speed of light. For example, the speed of light in the atmosphere and the speed of light in the living body may differ, for example, by about 1.4 times, and biometric information using the ToF sensor may be used for correcting an error of about 1.4 times.

In an embodiment, the structured light sensor may emit a plurality of structured lights having different designated patterns (e.g., patterns of structured light) to the external object (e.g., a user of the electronic device 201). The structured light sensor may obtain a pattern of each of the plurality of emitted structured lights. While the plurality of structured lights emitted to the external object are reflected from the external object, distortion of a predetermined pattern may be formed. The structured light sensor may recognize the external object based on distortion of a formed predetermined pattern, and measure a distance between the electronic device 201 and the external object.

The disclosure is not limited thereto, and the depth sensor 241 may include a proximity sensor based on an amount of light. The proximity sensor may include an emitter and a receiver. When a current of predetermined intensity flows from the emitter of the proximity sensor, light emitted through a light emitting diode (LED) may be reflected by the external object to be received by the receiver (e.g., photodiode). For example, as a distance between the electronic device 201 and the external object is included within a specified distance or light emitted through the LED is closer to white, an amount of light received from the receiver may increase. The distance between the electronic device 201 and the external object may be calculated based on an amount of light received from the receiver.

In an embodiment, the biosensor 243 may obtain a bio-signal of a measurement point. For example, the biosensor 243 may include a photoplethysmograph (PPG) sensor and/or an electrocardiograph (ECG) sensor. The measurement point may include a part of the user's body (e.g., fingertip and/or wrist). The biosensor 243 may obtain information on the user's heartbeat from the part of the user's body.

In an embodiment, the PPG sensor may include an emitter and a receiver. The emitter and the receiver may be configured with at least one element. For example, the emitter may be configured with an LED of R (red)/G (green)/B (blue)/IR (infrared). The receiver may include at least one photodiode capable of receiving various bands. The PPG sensor may measure light reflected from the external object. The PPG sensor may be disposed at a rear surface of the electronic device 201 or may be configured at a front surface of the electronic device 201 using a proximity sensor and/or an image sensor. When the PPG sensor is configured as a proximity sensor and/or an image sensor, a PPG signal may be obtained using an emitter, a receiver, and/or an image sensor of the proximity sensor.

In another embodiment, the PPG sensor may be disposed under the display 251 of the electronic device 201. When the PPG sensor is disposed under the display 251, the emitter for obtaining the PPG signal may use a pixel of the display. When the PPG sensor is disposed under the display 251, the receiver for obtaining the PPG signal may be disposed under the display 251 or may be configured in a form in which the receiver is included in the pixel. When the PPG sensor according to another embodiment is disposed under the display 251, the user's accessibility for obtaining bio-signals is easy, so that the user experience can be improved.

In an embodiment, the ECG sensor may measure an electrocardiogram. The ECG sensor may detect an electrical signal generated when the heart beats to measure a speed and timing of the heartbeat. When an electrocardiogram is measured using a pulse wave velocity (PWV) method, the ECG sensor may measure the timing of ejection from the heart, and the PPG sensor may measure the timing of a pulse wave arriving at the body part. A blood flow velocity may be estimated using the time difference between timings measured by the ECG sensor and the PPG sensor.

In an embodiment, the ECG sensor may be made of a conductive material. When the ECG sensor is made of a conductive material, the ECG sensor may measure a potential change through an electrode to obtain an ECG signal. The ECG sensor may be mounted as an indium tin oxide film (ITO) on an upper side surface of the display 251. The disclosure is not limited thereto, and the ECG sensor may be attached as an electrode or a transparent electrode to a side surface or a rear surface of the electronic device 201, and measure ECG information through the electrode or the transparent electrode attached to the side surface or the rear surface of the electronic device 201.

In an embodiment, the motion sensor 245 may obtain motion information of the electronic device 201. The motion information of the electronic device 201 may be used for improving accuracy of a PPG signal obtained from the biosensor 243, for example, the PPG sensor.

In another embodiment, the motion sensor 245 may operate as a ballistocardiogram (BCG) sensor. For example, when the electronic device 201 is located at the user's biometric reference point, for example, the heart, the motion sensor 245 operating as a BCG sensor may detect a tremor due to a heartbeat, and measure the degree and time of the heartbeat based on the tremor.

According to an embodiment, the touch screen display 250 (e.g., the display module 160 of FIG. 1) may be integrally configured including the display 251 and a touch panel 253.

According to an embodiment, the touch screen display 250 may display a screen according to execution of a specific application, for example, a health application under the control of the processor 260. When a signal for measuring biometric information is detected under the control of the processor 260, the touch screen display 250 may display a user interface including a guide for obtaining biometric information. For example, the touch screen display 250 may display a user interface including guide information (e.g., guide information for inducing the user to stretch out an arm (e.g., stretch out an arm to the maximum) and take a picture) for inducing the user to take a reference posture in order to calculate a distance between a measurement point and a biometric reference point under the control of the processor 260. The touch screen display 250 may display a user interface including a guide for obtaining a bio-signal from the measurement point under the control of the processor 260. For example, the touch screen display 250 may display guide information for inducing the user to comfortably measure while seating on a chair and placing an arm on a desk under the control of the processor 260.

According to an embodiment, the processor 260 (e.g., the processor 120 of FIG. 1) may control an overall operation of the electronic device 201 and a signal flow between internal components of the electronic device 201, perform data processing, and control the supply of power from the battery to the components.

According to an embodiment, when the processor 260 detects a signal for measuring biometric information, for example, a signal (e.g., blood pressure measurement) for obtaining biometric information according to execution of a specific application (e.g., health application), the processor 260 may obtain depth information on the user using the sensor unit 240, for example, the depth sensor 241. The processor 260 may determine a location of the biometric reference point, for example, the heart based on the obtained depth information on the user.

In an embodiment, the processor 260 may obtain a bio-signal of the measurement point, for example, a part of the user's body (e.g., finger and/or wrist) using the sensor unit 240, for example, the depth sensor 241. The disclosure is not limited thereto, and the processor 260 may obtain a bio-signal of the measurement point, for example, a part of the user's body from the biosensor 243.

In an embodiment, the processor 260 may calculate a distance between the measurement point and the biometric reference point. For example, the processor 260 may calculate a distance using the emitter and the receiver included in the sensor unit 240, for example, the depth sensor 241, calculate a distance based on a change in a light pattern, and/or calculate a distance based on a phase change of light having a specific frequency.

In an embodiment, the processor 260 may correct biometric data of the user based on the calculated distance and the bio-signal. For example, the biometric data may include blood pressure information and/or blood sugar information.

Figure 3:
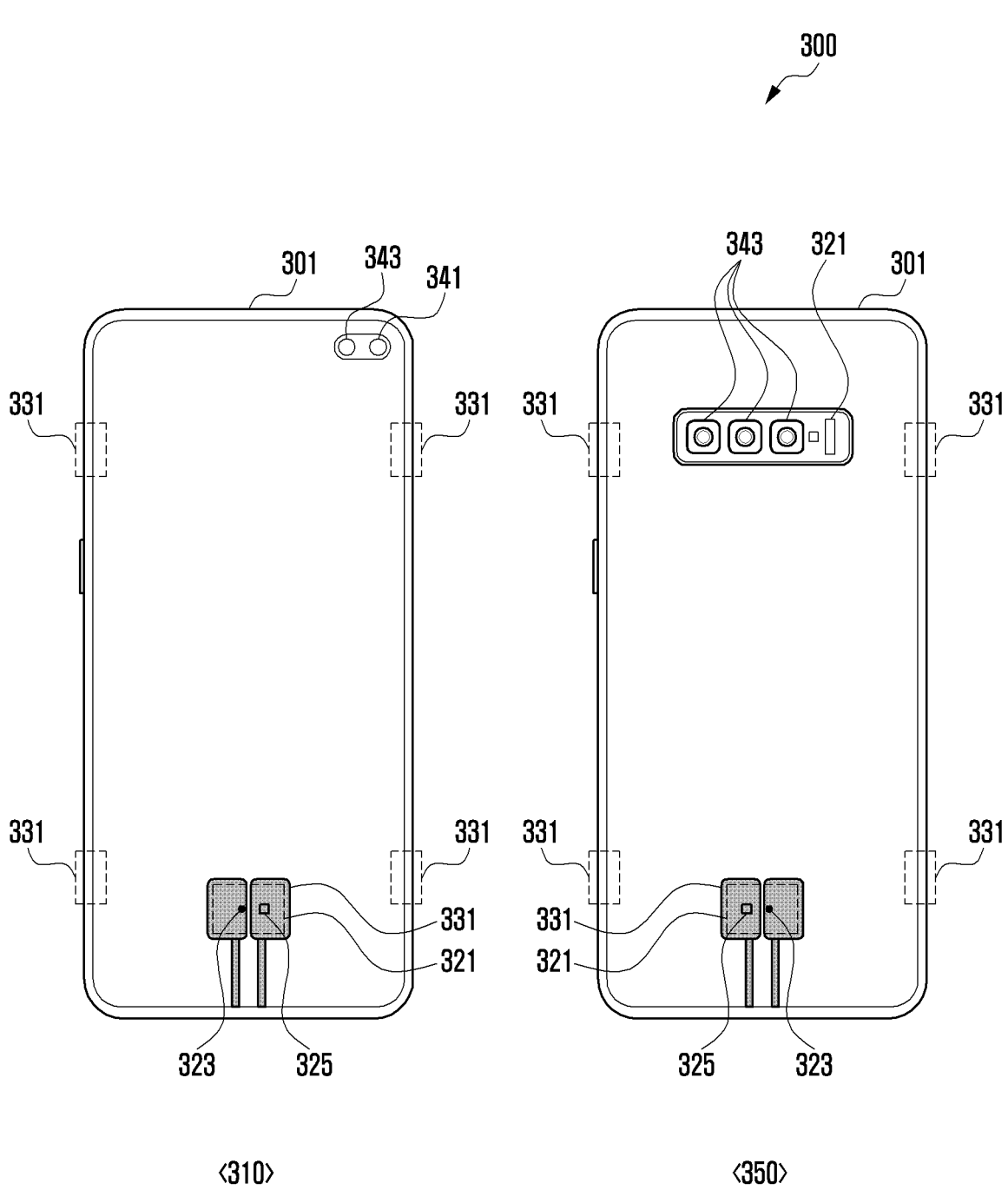
FIG. 3 is a diagram illustrating at least one sensor unit provided in an electronic device according to various embodiments.

FIG. 3 is a diagram 300 illustrating at least one sensor unit provided in an electronic device according to various embodiments.

Referring to FIG. 3, an electronic device 301 (e.g., the electronic device 201 of FIG. 2) may include at least one sensor unit (e.g., the sensor unit 240 of FIG. 2). At least one sensor unit may include a biosensor (e.g., the biosensor 243 of FIG. 2), for example, a photoplethysmograph (PPG) sensor 321, an electrocardiograph (ECG) sensor 331, and/or a depth sensor 341 (e.g., the depth sensor 241 of FIG. 2).

In an embodiment, the PPG sensor 321 may be configured using a proximity sensor and/or an image sensor at the front surface or the rear surface of the electronic device 301, as illustrated in reference numerals <310> and <350>. When the PPG sensor 321 is configured as a proximity sensor and/or an image sensor, the PPG sensor 321 may obtain a PPG signal using an emitter and a receiver of the proximity sensor, and/or an image sensor.

In an embodiment, the PPG sensor 321 may be disposed under the display (e.g., the display 251 of FIG. 2) of the electronic device 301. When the PPG sensor 321 is disposed under the display, an emitter 323 and a receiver 325 for obtaining a PPG signal may be configured as pixels of the display.

In an embodiment, in order to measure a heartbeat of the user of the electronic device 301, the PPG sensor 321 may be exposed through a part of the rear surface or the front surface of the electronic device 301. The PPG sensor 321 may be disposed at the upper end of the rear surface of the electronic device 301 so that the user may contact a heart rate sensor with a part (e.g., finger) of the user's body in a state in which the user grips the electronic device 301. However, the disclosure is not limited thereto, and the PPG sensor 321 may be disposed in various locations so that a part of the user's body may contact the PPG sensor 321.

In an embodiment, the ECG sensor 331 may measure an electrocardiogram. The ECG sensor 331 may be made of a conductive material or may be mounted as transparent electrodes on an upper side surface and/or a lower side surface of the display and a side surface and/or a rear surface of the electronic device 301.

In an embodiment, the depth sensor 341 may obtain depth information on the external object and/or calculate distance information between the electronic device 301 and the external object, for example, the user. For example, the depth sensor 341 may include an emitter and a receiver. For example, the emitter included in the depth sensor 341 may emit visible light and/or IR. The receiver included in the depth sensor 341 may detect light reflected back and applied thereon after the light emitted from the emitter reaches an external object. For example, reflected and incident light may be received in the form of a dot, a plane, or a pattern. The depth sensor 341 may measure a distance between the electronic device 301 and a specific point (e.g., eye, nose, and/or mouth) of the external object based on the received dot form. In another embodiment, the depth sensor 341 may estimate a distance between the electronic device 301 and the external object and a shape of the external object based on the received plane form (or pattern form).

In an embodiment, the depth sensor 341 may be disposed at the front surface and/or the rear surface of the electronic device 301. The depth sensor 341 may be separately provided at the front surface and/or the rear surface of the electronic device 301 or may be included in a camera 343 (e.g., the camera 220 of FIG. 2).

Figure 4:
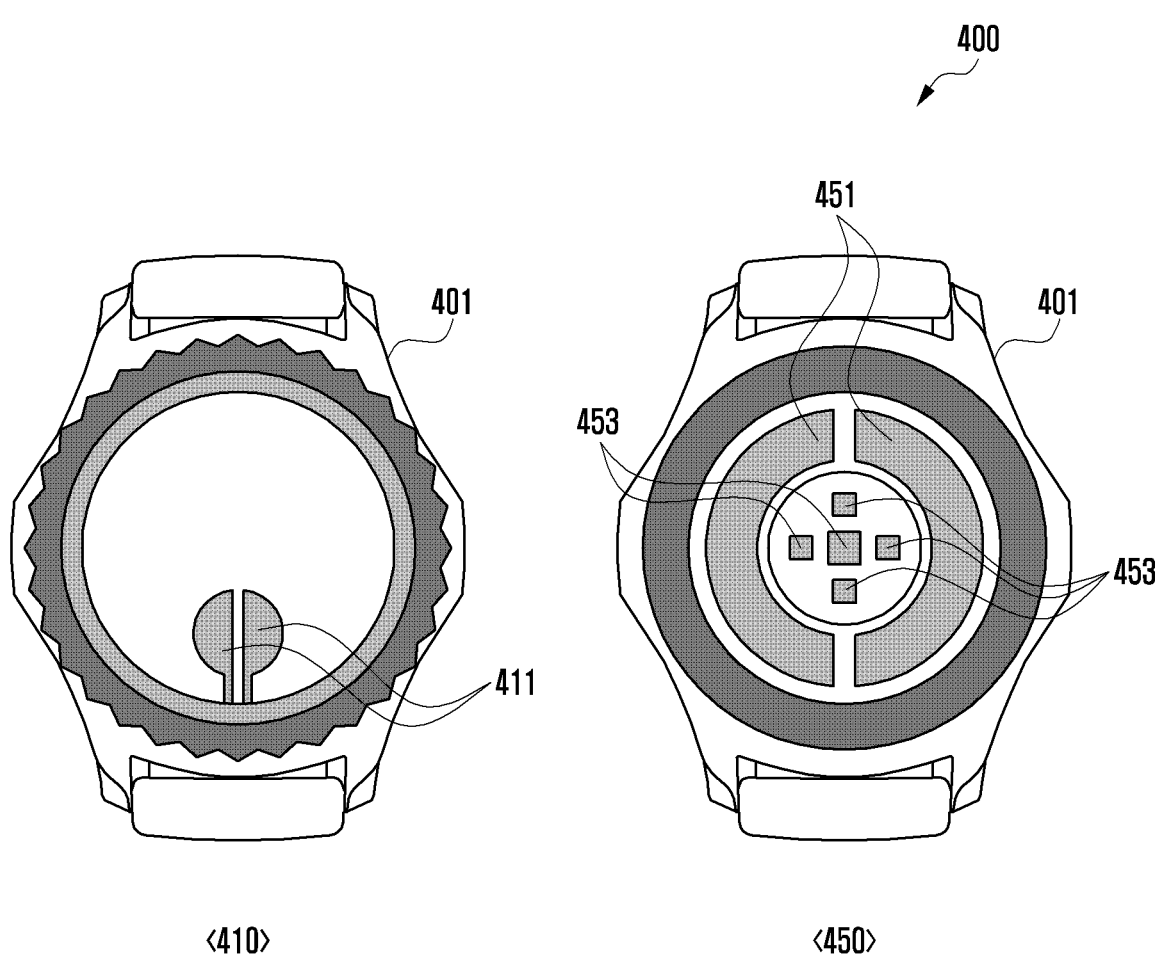
FIG. 4 is a diagram illustrating at least one sensor unit provided in a wearable device according to various embodiments.

FIG. 4 is a diagram 400 illustrating at least one sensor unit provided in a wearable device according to various embodiments.

Referring to FIG. 4, a housing of a wearable device 401 (e.g., smart watch) may be implemented in various forms. For example, the housing of the wearable device 401 may be implemented in a circular shape that can be attached to a part (e.g., wrist) of the user's body, as illustrated in reference numerals <410> and <450>. However, the disclosure is not limited thereto, and the housing of the wearable device 401 may be implemented in a rectangular shape, a square shape, or an oval shape.

In an embodiment, the wearable device 401 may include a biosensor (e.g., the biosensor 243 of FIG. 2) for measuring the heartbeat of a user wearing the wearable device 401. The biosensor may include a PPG sensor 453 (e.g., the PPG sensor 321 of FIG. 3) and/or ECG sensors 411 and 451 (e.g., the ECG sensor 331 of FIG. 3).

Because the PPG sensor 453 and the ECG sensors 411 and 451 according to the embodiment of FIG. 4 perform the same function as that of the PPG sensor 321 and the ECG sensor 331 according to the embodiment of FIG. 3, a detailed description thereof may be substituted with the description of FIG. 3.

In an embodiment, the biosensors 411, 451, and 453 of the wearable device 401 may be disposed at the rear surface or the front surface of the wearable device 401 in order to measure a user's heartbeat. The biosensors 411, 451, and 453 may be exposed through a part of the rear surface or the front surface of the wearable device 401 in order to measure the heartbeat of the user. The rear surface may be a surface disposed in a direction opposite to that of the front surface. The rear surface or the front surface may be configured to be in contact with a part of the user's body. The biosensors 411, 451, and 453 may be exposed through a part of the rear surface or the front surface of the wearable device 401 so as to be in contact with a part of the user's body, thereby measuring the user's heartbeat.

In an embodiment, the biosensor 411 may be mounted as an indium tin oxide film (ITO) on the front surface of the wearable device 401, as illustrated in reference number <410>.

Although not illustrated in FIG. 4 according to an embodiment, the wearable device 401 may further include a depth sensor (e.g., the depth sensor 241 of FIG. 2). The depth sensor may be disposed at the front surface and/or a side surface of the wearable device 401.

Figure 5:
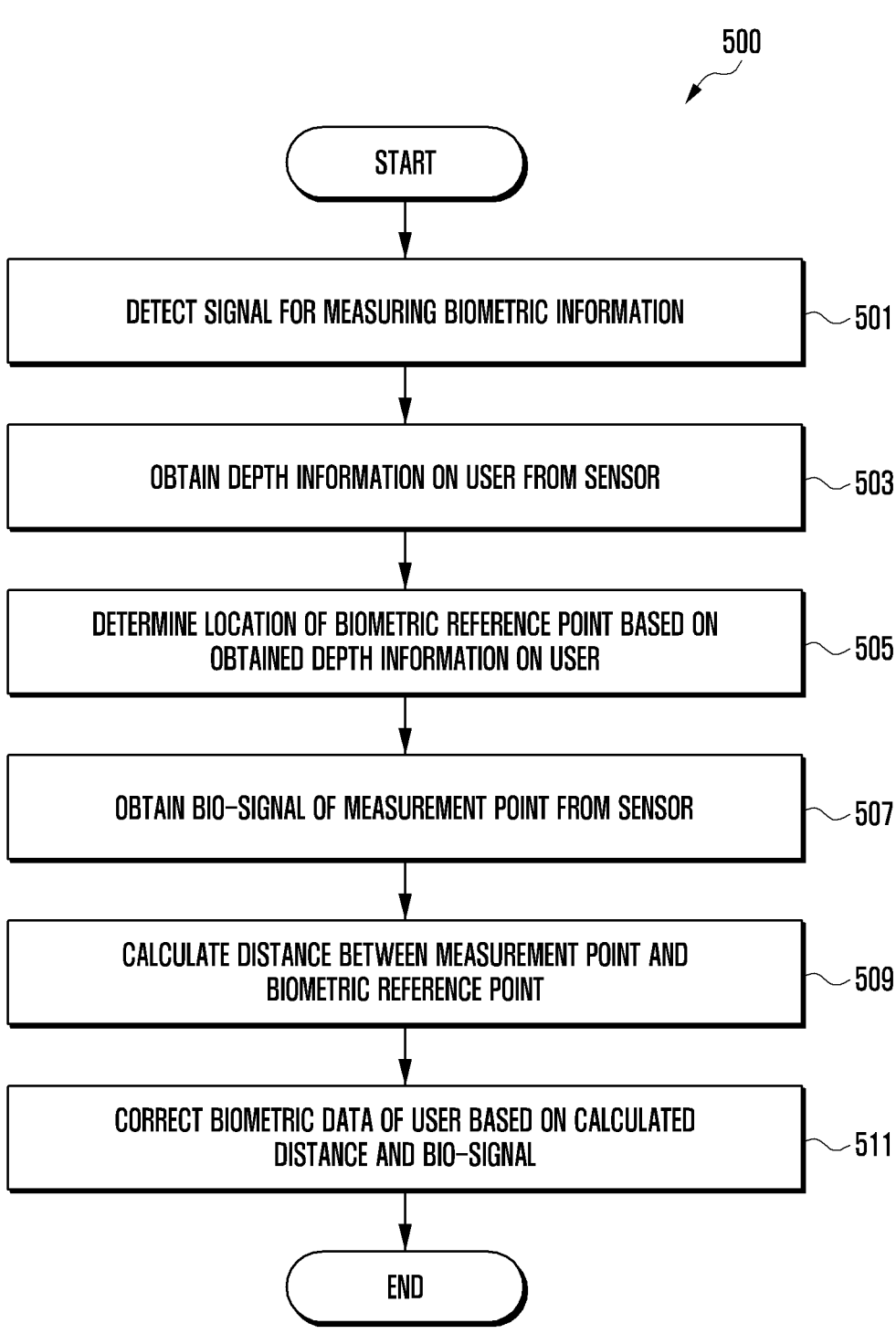
FIG. 5 is a flowchart illustrating a method in which an electronic device obtains a distance between the electronic device and a user and biometric data using a sensor according to various embodiments.

FIG. 5 is a flowchart 500 illustrating a method in which an electronic device obtains a distance between the electronic device and a user and biometric data using a sensor according to various embodiments.

Referring to FIG. 5, the processor (e.g., the processor 260 of FIG. 2) may detect a signal for measuring biometric information in operation 501. For example, a signal for measuring biometric information may be detected when a specific application (e.g., health application) is executed.

In an embodiment, when a signal for measuring biometric information is detected, the processor 260 may display a first user interface including a guide for obtaining biometric information on the display (e.g., the display 251 of FIG. 2). The first user interface may include guide information (e.g., guide information for inducing the user to stretch out an arm and take a picture) for guiding a user to take a reference posture in order to calculate a distance between the measurement point and the biometric reference point in operation 509 to be described later.

In an embodiment, the processor 260 may obtain depth information on the user from the sensor (e.g., the sensor unit 240 of FIG. 2) in operation 503. For example, the sensor may include a depth sensor (e.g., the depth sensor 241 of FIG. 2).

In an embodiment, the electronic device (e.g., the electronic device 201 of FIG. 2) may include at least one depth sensor, and the at least one depth sensor may be disposed at the front surface and/or the rear surface of the electronic device.

In an embodiment, the processor 260 may obtain depth information on the user using the depth sensor, for example, the depth sensor disposed at the front surface of the electronic device. For example, the depth sensor may project a 2D pattern onto the user, analyze the degree of deformation of the pattern, and obtain a 3D depth image or a surface of the user based on the analyzed degree of deformation. The processor 260 may obtain information on a location of the user's face, eyes, nose, and mouth and/or upper body depth information based on the obtained depth image. The disclosure is not limited thereto, and a plurality of structured lights having different specified patterns (e.g., structured light patterns) are emitted to an external object using a structured light sensor, which is one of the depth sensors, and a pattern of each of the plurality of emitted structured light may be obtained. The structured light sensor may recognize an external object based on distortion of a predetermined pattern formed while a plurality of emitted structured lights are reflected from the external object. The structured light sensor may obtain information on a location of a recognized external object, for example, a user's face, eyes, nose, and mouth, and/or upper body depth information based on distortion of a predetermined pattern.

In an embodiment, in operation 505, the processor 260 may determine a location of the biometric reference point based on the obtained depth information on the user. For example, the biometric reference point may include a heart. However, the disclosure is not limited thereto.

In an embodiment, the processor 260 may determine locations of the user's face, eyes, nose, and mouth using the depth sensor, and determine a biometric reference point, for example, a location of the heart based on the locations.

In an embodiment, in operation 507, the processor 260 may obtain a bio-signal of the measurement point from the sensor. For example, the processor 260 may obtain a bio-signal of a measurement point using the depth sensor, for example, the depth sensor disposed at the rear surface of the electronic device.

In an embodiment, the measurement point may include a part of the user's body, and the part of the user's body may include a fingertip or a wrist. The processor 260 may obtain information related to the user's heartbeat from a part of the user's body using the sensor, for example, the depth sensor. The heart rate-related information may include a heart rate per second, a heart rate cycle, and/or heart rate intensity.

In another embodiment, the processor 260 may obtain information related to the user's heartbeat using the depth sensor disposed at the front surface of the electronic device. For example, the processor 260 may measure information related to a user's heartbeat using a camera (e.g., the camera 220 of FIG. 2) and an IR light source included in the depth sensor. The depth sensor may include an emitter and a receiver. The emitter of the depth sensor may emit IR to an external object, for example, a part (e.g., the user's face) of the user's body. The processor 260 may sequentially capture a value reflected back after reaching a part of the user's body using the camera 220 (or image sensor). The processor 260 may obtain information related to a heartbeat according to a change amount of a signal in which hemoglobin of blood contained in blood vessels of a part of an external object, for example, the user's body is absorbed based on at least one image captured by the camera 220.

In an embodiment, the bio-signal of the user's measurement point may be accurately obtained using the depth sensor disposed at the front surface of the electronic device as well as the depth sensor disposed at the rear surface of the electronic device.

In various embodiments, the operation of obtaining information related to the user's heartbeat using the depth sensor disposed at the front surface of the electronic device may be omitted.

In an embodiment, the processor 260 may display a second user interface including a guide for obtaining the bio-signal from the measurement point on the display. For example, the second user interface may include guide information for inducing the user to comfortably measure the bio-signal while seating on a chair and placing an arm on a desk in order to accurately obtain the bio-signal.

In an embodiment, the processor 260 may calculate a distance between the measurement point and the biometric reference point in operation 509. For example, the processor 260 may calculate a distance using the emitter and the receiver included in the sensor, calculate a distance based on a change in a pattern of light, and/or calculate a distance based on a phase change of light at a specific frequency. However, the disclosure is not limited thereto.

In an embodiment, the processor 260 may estimate a biometric reference point of the measurement point, for example, a height relative to the heart based on an angle at which the user's face is sensed, and calculate a distance between the depth sensor and the user based on this. For example, the processor 260 may estimate a relative distance between the electronic device and the user based on distance information between the user's two eyes or location information of the eyes and the nose. In another embodiment, the processor 260 may obtain an absolute location of at least one point (e.g., eyes, nose, and/or mouth in the user's face) based on depth information obtained from the depth sensor, and calculate a distance to the biometric reference point based on the obtained absolute location.

In an embodiment, the processor 260 may estimate a length of the user's arm and a length of blood flow from the heart to the measurement point based on the calculated distance.

In an embodiment, the processor 260 may correct biometric data of the user based on the calculated distance and the bio-signal in operation 511. In an embodiment, the biometric data of the user may be stored in the memory (e.g., the memory 230 of FIG. 2), and the biometric data stored in the memory may be corrected based on the calculated distance and the bio-signal. For example, the biometric data may include blood pressure information and/or blood sugar information.

FIG. 6 is a flowchart 600 illustrating a method in which an electronic device obtains a distance between the electronic device and a user and biometric data using a plurality of sensors according to various embodiments.

Because operations 601 to 605 according to an embodiment are the same as the foregoing operations 501 to 505 of FIG. 5, and operations 609 and 611 are the same as the foregoing operations 509 and 511 of FIG. 5, a detailed description thereof may be substituted with the description related to FIG. 5.

Referring to FIG. 6, when a signal for measuring biometric information is detected in operation 601, the processor (e.g., the processor 260 of FIG. 2) may obtain depth information on the user from a first sensor in operation 603. For example, the first sensor may include a depth sensor (e.g., the depth sensor 241 of FIG. 2).

In an embodiment, in operation 605, the processor 260 may determine a location of the biometric reference point based on the obtained depth information on the user. For example, the biometric reference point may include a heart. However, the disclosure is not limited thereto.

In an embodiment, in operation 607, the processor 260 may obtain a bio-signal of the measurement point from a second sensor. For example, the measurement point may include a part of the user's body, and the part of the user's body may include a fingertip or a wrist. The processor 260 may obtain information related to the user's heartbeat from a part of the user's body using the second sensor. The heart rate-related information may include a heart rate per second, a heart rate cycle, and/or heart rate intensity.

In an embodiment, the second sensor may include a biosensor (e.g., the biosensor 243 of FIG. 2) (e.g., PPG sensor, ECG sensor), and/or a ToF sensor.

In an embodiment, when the electronic device is held by the user, the processor 260 may receive a PPG signal from a part of the body, for example, a fingertip, and the other part of the body may receive an ECG signal. In an embodiment, when the PPG sensor and the ECG sensor configured with a transparent electrode are configured to overlap, the processor 260 may receive an ECG signal through the ECG sensor configured with the transparent electrode, and measure a pulse wave using the PPG sensor.

In an embodiment, the processor 260 may calculate a distance between the measurement point and the biometric reference point in operation 609. For example, the processor 260 may estimate a blood vessel length of the user in which a pulse measured using the first sensor has moved simultaneously with acquisition of the bio-signal of the measurement point from the second sensor in operation 607.

In an embodiment, the processor 260 may correct biometric data of the user based on the calculated distance and the bio-signal in operation 611.

In FIG. 6 according to an embodiment, when measuring biometric information on a measurement point using the second sensor provided in the electronic device, accuracy of biometric data measured in consideration of distance information (or blood flow length) calculated using the first sensor can increase. As biometric information unique to a user using the electronic device is measured through 3D face recognition using the first sensor (e.g., depth sensor), reliability of collected biometric information can increase.

FIG. 7 is a flowchart 700 illustrating a method in which an electronic device obtains biometric data using a plurality of sensors according to various embodiments.

In an embodiment described with reference to FIG. 7, it will be described on the assumption that that biometric data is a blood pressure value and a pulse wave velocity (PWV) method is used as a method of measuring a blood pressure. The PWV method may include a method of measuring a transmission speed of a waveform from a biometric reference point, for example, a heart to a measurement point, for example, a point (e.g., fingertip, wrist) at which a PPG signal is measured using a PPG sensor, an ECG sensor, or a BCG sensor.

Referring to FIG. 7, the processor (e.g., the processor 260 of FIG. 2) may detect a signal for measuring biometric information in operation 701.

In an embodiment, a signal for measuring biometric information may be detected when, for example, a blood pressure measurement service is executed as a specific application (e.g., health application) is executed. When a signal for measuring biometric information is detected, the processor 260 may output guide information for inducing the user to take a reference posture (e.g., guide information for guiding the user to stretch out an arm and take a picture) to the display (e.g., the display 251 of FIG. 2).

In an embodiment, in operation 703, the processor 260 may obtain depth information on the user using a first sensor. For example, the first sensor may include a depth sensor (e.g., the depth sensor 241 of FIG. 2). In operation 705, the processor 260 may determine a location of the user's heart based on the obtained depth information on the user.

In an embodiment, the processor 260 may calculate a distance between the electronic device and the user using the first sensor in operation 707. In an embodiment, the processor 260 may calculate a distance from a biometric reference point, for example, the heart to the measurement point, for example, a finger or a wrist. As biometric data is obtained based on the measured distance between the electronic device and the user or the distance from the heart to the measurement point, accuracy of a velocity in which blood flow ejected from the heart passes through the blood vessel, for example, a PWV may be improved. For example, the PWV method may include a method of measuring a blood pressure based on Equation 1.

$$PWV = \frac{BDC * \text{height}}{PTT} \qquad [\text{Equation 1}]$$

For example, the pulse transit time (PTT) may mean a time taken when a pulse moves from the heart to the wrist, and a body correlation factor (BDC) may be a variable set based on that a distance from a tip of a left hand to a tip of a right hand has a high correlation with a height when the arm is spread out in a straight line. For example, for an adult, the BDC may be 0.5.

In an embodiment, in operation 709, the processor 260 may obtain a bio-signal of the user using a second sensor. For example, the second sensor may include a PPG sensor, an ECG sensor, and/or a ToF sensor. However, the disclosure is not limited thereto, and a bio-signal of the user may be obtained using the first sensor, for example, the depth sensor.

In an embodiment, in operation 711, the processor 260 may estimate a blood flow distance from the heart for measuring a blood pressure to a measurement point at which the bio-signal is obtained based on the measured distance between the electronic device and the user. In operation 713, the processor 260 may estimate a pulse wave arrival time from the heart to the measurement point based on the obtained bio-signal. The processor 260 may estimate a blood flow velocity based on the pulse wave arrival time and the blood flow distance in operation 715, and correct a blood pressure value based on the blood flow velocity in operation 717.

Figure 8:
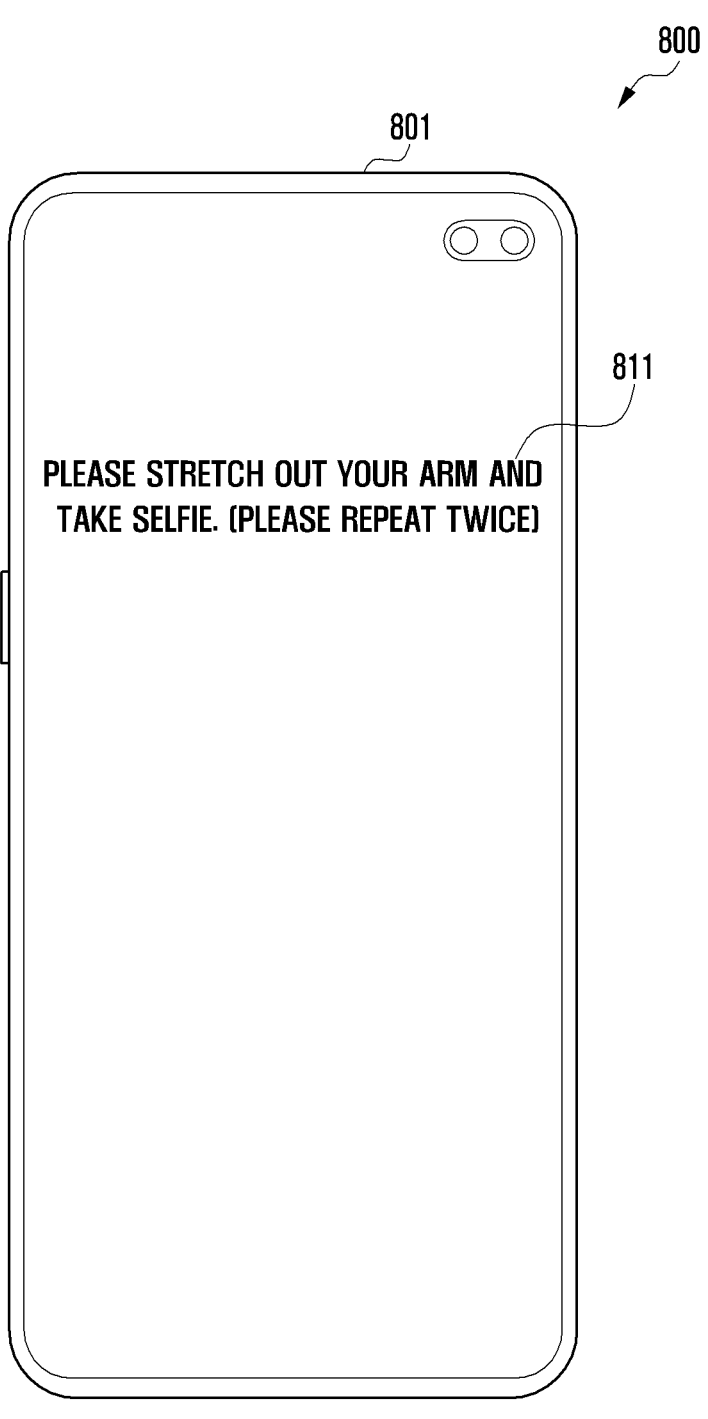
FIG. 8 is a diagram illustrating a user interface of an electronic device including guide information for guiding a user to take a reference posture in order to calculate a distance between the electronic device and the user according to various embodiments.

FIG. 8 is a diagram 800 illustrating a user interface of an electronic device including guide information for guiding a user to take a reference posture in order to calculate a distance between the electronic device and the user according to various embodiments.

Referring to FIG. 8, the processor (e.g., the processor 260 of FIG. 2) may display a user interface including guide information for inducing the user to take a reference posture on the display (e.g., the display 251 of FIG. 2) in order to calculate a distance between an electronic device 801 and the user in response to detection of a signal for measuring biometric information. For example, the processor 260 may output guide information, for example, please stretch out your arm and take a selfie." 811 for inducing the user to stretch out an arm and take a picture on the display 251 so that the distance between the electronic device 801 and the user is accurately measured (or so that a blood flow length from the heart to the measurement point is accurately measured).

In an embodiment, the processor 260 may further output, on the display 251, a user interface including guide information, for example, "please repeat twice" for inducing the user to repeatedly perform an operation of obtaining depth information on the user using the depth sensor (e.g., the depth sensor 241 of FIG. 2) in the reference posture.

In an embodiment, the processor 260 may accumulate a distance between the electronic device 801 and the user (or a distance between the measurement point and the biometric reference point) and store (e.g., update) the distance in the memory (e.g., the memory 230 of FIG. 2) based on the depth information obtained using the depth sensor according to the guide information. The processor 260 may determine distance information having a maximum value as reference distance information based on distance information stored in the memory.

In an embodiment, when the calculated distance between the electronic device 801 and the user (or the distance between the measurement point and the biometric reference point) is included within a specified range of the reference distance information, the processor 260 may perform an operation of correcting biometric data. When the calculated distance between the electronic device 801 and the user (or the distance between the measurement point and the biometric reference point) is not included within a specified range of the reference distance information, the processor 260 may determine that the user does not take a reference posture and output a user interface including guide information for inducing the user to take a reference posture.

Figure 9:
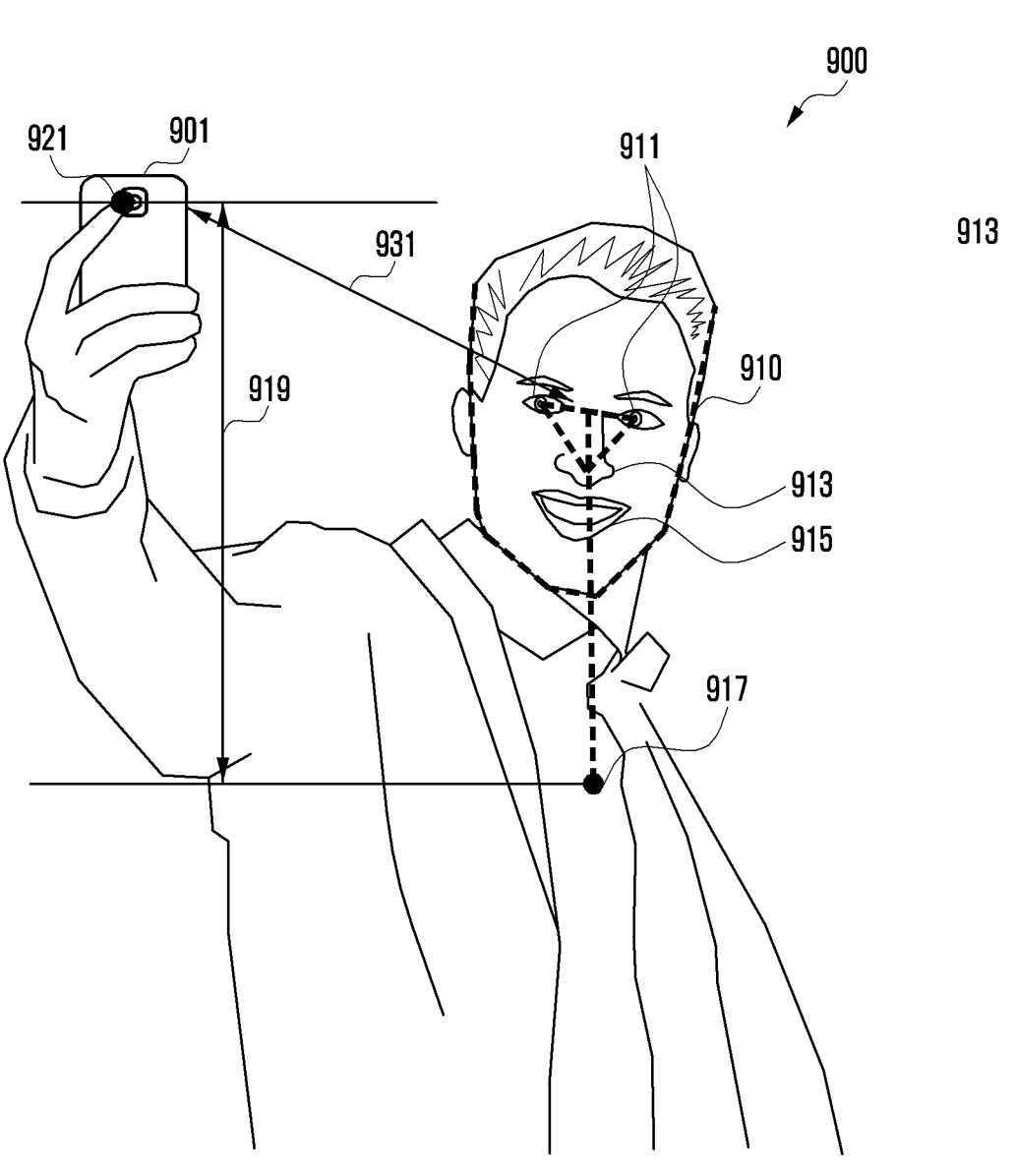
FIG. 9 is a diagram illustrating a method in which an electronic device measures a distance between the electronic device and a user using a sensor according to various embodiments.

FIG. 9 is a diagram 900 illustrating a method in which an electronic device measures a distance between an electronic device and a user using a sensor according to various embodiments.

Referring to FIG. 9, the processor (e.g., the processor 260 of FIG. 2) may determine a location of the user's face 910 and a location of eyes 911, a nose 913, and a mouth 915 of the user in the user's face 910 by sensing the user in a reference posture (e.g., a posture in which the user stretches out an arm) using the depth sensor (e.g., the depth sensor 241 of FIG. 2) and determine a location of a biometric reference posture, for example, a location of a heart 917 based on the locations.

In an embodiment, the processor 260 may receive a bio-signal of a measurement point 921 from the depth sensor 241 and/or the biosensor (e.g., the biosensor 243 of FIG. 2) (e.g., the PPG sensor (e.g., the PPG sensor 321 and an ECG sensor (e.g., the ECG sensor 331 of FIG. 3) of FIG. 3).

In an embodiment, the processor 260 may estimate a relative height 919 of the measurement point 921 (e.g., the fingertip of the user) compared to the heart 917 based on an angle at which the face 910 is sensed. The processor 260 may calculate a distance 931 between the depth sensor 241 and the user. For example, arm lengths according to gender and age may be stored in the memory (e.g., the memory 230 of FIG. 2) for each range. The processor 260 may calculate a distance between an electronic device 901 and the heart 917 based on the length of the arm stored in the memory.

In another embodiment, the user's face shape information for personal authentication (e.g., face recognition) may be pre-stored in the memory 230. When the user's face shape information is stored in the memory 230, the processor 260 may omit an operation of determining a location of the biometric reference point, for example, a location of the heart 917 based on a location of the user's face 910 determined by sensing the user and locations of eyes 911, a nose 913, and a mouth 915 in the user's face 910. For example, the processor 260 may determine a distance between the user's eyes and a distance between the nose and mouth of the user based on face shape information previously stored in the memory 230. The processor 260 may determine a relative distance 931 between the depth sensor 241 and the user based on a distance between the user's eyes and a distance between the nose and the mouth determined based on the stored face shape information. The processor 260 may estimate a location of the heart 917 and/or a relative height 919 of the measurement point 921 compared to the heart 917 according to the relative distance 931.

In an embodiment, the processor 260 may update arm length information previously stored in the memory 230 to the obtained arm length information. For example, the processor 260 may accumulate a distance between the electronic device 901 and the user (or a distance between the measurement point 921 and the biometric reference point 917) and store (e.g., update) the distance in the memory based on depth information obtained using the depth sensor 241. The processor 260 may determine distance information having a maximum value as reference distance information based on the distance information stored in the memory 230. In an embodiment, when the distance between the measurement point 921 and the biometric reference point 917 is included within a specified range of the maximum value determined as the reference distance information, the processor 260 may perform an operation of correcting the biometric data. In an embodiment, when the distance between the measurement point 921 and the biometric reference point 917 is not included within a specified range of the maximum value determined as the reference distance information, the processor 260 may display a user interface including guide information (e.g., guide information for inducing the user to stretch out an arm and take a picture) for inducing to take a reference posture a user interface including information on the display (e.g., the display 251 of FIG. 2).

Figure 10:
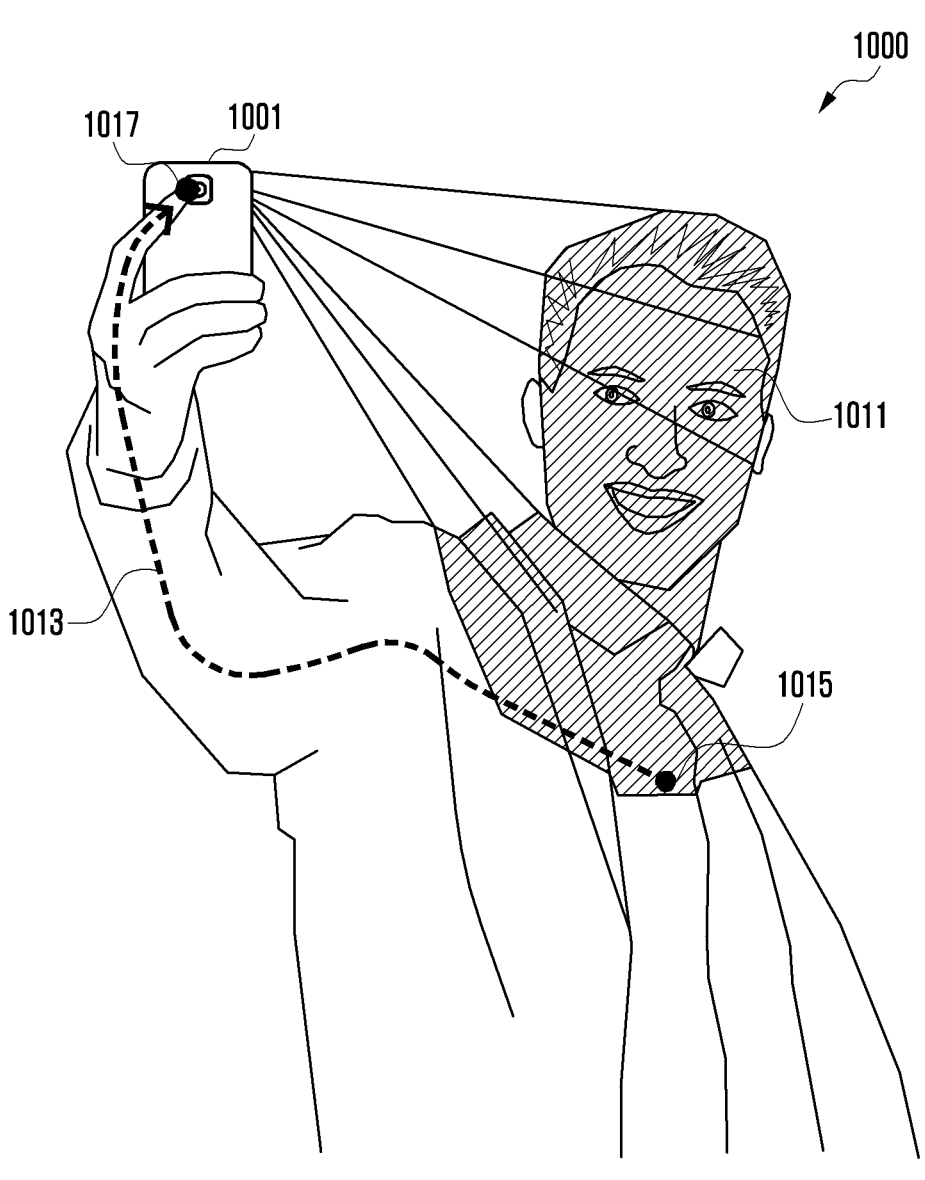
FIG. 10 is a diagram illustrating a method in which an electronic device corrects a user's biometric data after measuring a distance between the electronic device and the user using a sensor according to various embodiments.

FIG. 10 is a diagram 1000 illustrating a method in which an electronic device corrects a user's biometric data after measuring a distance between the electronic device and the user using a sensor according to various embodiments.

FIG. 10 according to an embodiment illustrates a path 1013 in which a waveform is transmitted through a blood vessel formed between a heart 1015 and a measurement point 1017 (e.g., a user's fingertip) when a blood pressure is measured.

Referring to FIG. 10, the processor (e.g., the processor 260 of FIG. 2) may estimate a length of the user's arm and a blood flow length 1013 from the heart 1015 to the measurement point 1017 based on a distance between the depth sensor (e.g., the depth sensor 241 of FIG. 2) calculated according to the embodiment of FIG. 9 and the user. For example, the processor 260 may estimate a speed at which a waveform generated from the heart 1015 reaches the measurement point 1017 based on the calculated distance. In an embodiment, the processor 260 may correct biometric data, for example, blood pressure information of the user based on a speed at which the estimated waveform generated from the heart 1015 reaches the measurement point 1017.

In an embodiment, the calculated distances between the electronic devices 901 and 1001 and the hearts 917 and 1015 may be updated whenever a signal for obtaining biometric information is detected. The updated distance between the electronic devices 901 and 1001 and the hearts 917 and 1015 may not only improve a pulse movement path value, but may also be used for improving blood pressure information accordingly.

Figure 11:
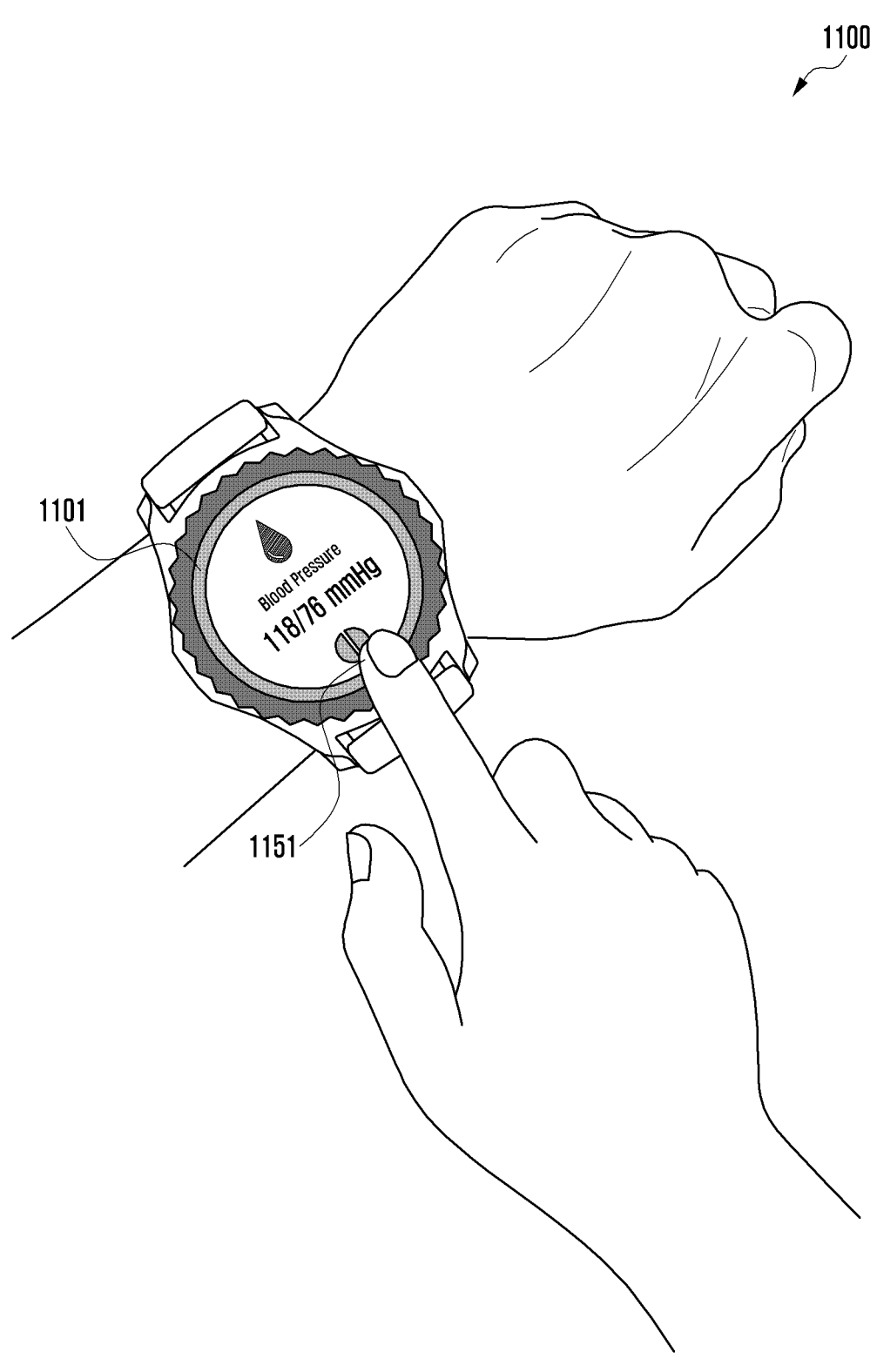
FIG. 11 is a diagram illustrating a method of measuring a distance between a wearable device and a user using a sensor, and correcting the user's biometric data based on the measured distance according to various embodiments.

FIG. 11 is a diagram 1100 illustrating a method of measuring a distance between a wearable device and a user using a sensor, and correcting the user's biometric data based on the measured distance according to various embodiments.

In FIG. 11, it will be described on the assumption that the wearable device is a smart watch 1101. However, the disclosure is not limited thereto.

Referring to FIG. 11, a smart watch 1101 may include a depth sensor. The depth sensor may be provided at a front surface or a side surface of the smart watch 1101. In an embodiment, the depth sensor may be included in the camera. The processor (e.g., the processor 260 of FIG. 2) may obtain depth information on the user in a reference posture (e.g., a state with an arm stretched) using the depth sensor. The processor 260 may determine a location of a biometric reference point, for example, a heart (e.g., the heart 917 of FIG. 9) based on the obtained depth information.

In another embodiment, the smart watch 1101 may be paired with an electronic device (e.g., the electronic device 201 of FIG. 2). In this case, the smart watch 1101 may receive guide information (e.g., guide information for inducing the user to stretch out an arm and take a picture) for inducing a user to take a reference posture from the electronic device 201 and/or guide information (e.g., guide information for inducing the user to comfortably measure while seating on a chair and placing an arm on a desk) for obtaining a bio-signal from the measurement point, and display the guide information on the display. By providing the guide information, the user may measure a bio-signal through the smart watch 1101 in a posture that can accurately obtain bio-data.

In an embodiment, the processor (e.g., the processor 260 of FIG. 2) may measure 1151 a blood pressure using a biosensor, for example, a PPG sensor (e.g., the PPG sensor 453 of FIG. 4) and/or an ECG sensor (e.g., the ECG sensors 411 and 451 of FIG. 4). For example, the PPG sensor may be provided at a rear surface of the smart watch 1101, for example, at a surface in contact with the user's wrist. The ECG sensor may be provided in the form of an electrode using transparent ITO at a front surface and a rear surface of the smart watch 1101.

In an embodiment, the processor 260 may calculate a distance between the smart watch 1101 and the user's biometric reference point, for example, the heart, and estimate the user's arm length based on the calculated distance. The processor 260 may correct biometric data of the user based on the calculated distance (or the user's arm length) and the bio-signal.

According to an embodiment described with reference to FIGS. 2 to 11, when biometric data is obtained using a distance between the measurement point and the biometric reference point, accurate biometric data may be obtained, compared to when the distance is not considered. Because a length of an arm of each user is different and a length of a blood vessel is also different according to a body configuration of each user, the measured arm length of the user is further considered; thus, it may be helpful to correct biometric data, for example, blood pressure information. According to various embodiments of the disclosure, as a biometric reference point, for example, a relative location between a heart and a measurement point may be known, blood pressure information can be accurately corrected.

The electronic device according to certain embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that certain embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. The term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to certain embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to certain embodiments, each component (e.g., a module or a program) of the above-described components may include a single entity or multiple entities. According to certain embodiments, one or more of the above-described components may be omitted, or one or more other components may be added. Alternatively or additionally, a plurality of components (e.g., modules or programs) may be integrated into a single component. In such a case, according to certain embodiments, the integrated component may still perform one or more functions of each of the plurality of components in the same or similar manner as they are performed by a corresponding one of the plurality of components before the integration. According to certain embodiments, operations performed by the module, the program, or another component may be carried out sequentially, in parallel, repeatedly, or heuristically, or one or more of the operations may be executed in a different order or omitted, or one or more other operations may be added.

The invention claimed is:

1. An electronic device, comprising:
a depth sensor;
a biometric sensor;
memory storing instructions; and
a processor,
wherein the instructions, when executed by the processor, cause the electronic device to:
detect a signal for measuring biometric information,
obtain, in response to the signal, depth information of a user of the electronic device from the depth sensor, wherein the depth information includes information for at least one of a location of a face, eyes, nose, mouth, or upper body of the user,
determine, as a point corresponding to the user's heart, a biometric reference point identified based on the obtained depth information,
obtain the biometric information of the user's heart from the biometric sensor based on a part of the user's body being in contact with the biometric sensor,
calculate, using the depth sensor, a distance between the part of the user's body in contact with the biometric sensor and the user's heart,
determine a blood vessel length between the part of the user's body and the user's heart based on the calculated distance, and
correct the obtained biometric information based on the determined blood vessel length.

2. The electronic device of claim 1, further comprising an output device,
wherein the instructions, when executed by the processor, cause the electronic device to output, in response to the signal, guide information for inducing to taking of a reference posture through the output device in order to calculate the distance between the part of the user's body and the user's heart, and
wherein the output device comprises at least one of a touch screen display or an audio module.

3. The electronic device of claim 1, wherein the instructions, when executed by the processor, cause the electronic device to:
analyze the degree of deformation of a two-dimensional pattern projected onto the user using the depth sensor,
obtain a three-dimensional depth image of the user based on the analyzed degree of deformation, and obtain depth information on a specific point of the user based on the obtained depth image.

4. The electronic device of claim 3, wherein the instructions, when executed by the processor, cause the electronic device to determine, as the point corresponding to the user's heart, the biometric reference point based on the obtained depth information on the specific point of the user.

5. The electronic device of claim 1, wherein the memory is configured to store authentication information of the user, and wherein the instructions, when executed by the processor, cause the electronic device to:

determine, as the point corresponding to the user's heart, the biometric reference point based on the stored authentication information of the user, and calculate the distance between the part of the user's body and the user's heart based on the authentication information.

6. The electronic device of claim 1, wherein the memory is configured to store the biometric information, and wherein the instructions, when executed by the processor, cause the electronic device to:

correct the stored biometric information into the obtained biometric information based on the determined blood vessel length.

7. The electronic device of claim 1, further comprising a wireless communication circuit, wherein the instructions, when executed by the processor, cause the electronic device to transmit the calculated distance between the part of the user's body and the user's heart to an external electronic device through the wireless communication circuit.

8. The electronic device of claim 1, wherein the part of the user's body comprises at least one of the user's finger or wrist, and wherein the biometric information comprises at least one of blood pressure information or blood sugar information.

9. A method of an electronic device, the method comprising:

detecting a signal for measuring biometric information, obtaining, in response to the signal, depth information of a user of the electronic device from a depth sensor, wherein the depth information includes information for at least one of a location of a face, eyes, nose, mouth, or upper body of the user;

determining, as a point corresponding to the user's heart, a biometric reference point identified based on the obtained depth information;

obtaining the biometric information of the user's heart from a biometric sensor based on a part of the user's body being in contact with the biometric sensor;

calculating, using the depth sensor, a distance between the part of the user's body in contact with the biometric sensor and the user's heart;

determining a blood vessel length between the part of the user's body and the user's heart based on the calculated distance; and correcting the obtained biometric information based on the determined blood vessel length.

10. The method of claim 9, further comprising outputting, in response to the signal, guide information for inducing to taking of a reference posture through an output device in order to calculate the distance between the part of the user's body and the user's heart.

11. The method of claim 9, wherein the obtaining depth information of the user of the electronic device comprises:

analyzing the degree of deformation of a two-dimensional pattern projected onto the user using the depth sensor;

obtaining a three-dimensional depth image of the user based on the analyzed degree of deformation; and obtaining depth information on a specific point of the user based on the obtained depth image, wherein the determining the biometric reference point comprises determining the biometric reference point based on the obtained depth information on the specific point of the user.

12. The method of claim 9, wherein the calculating the distance comprises calculating the distance between the part of the user's body and the user's heart based on user authentication information stored in a memory, when authentication information of the user is stored in the memory, and wherein the correcting the biometric information comprises correcting biometric information stored in the memory into the obtained biometric information based on the determined blood vessel length.

\* \* \* \* \*